United States Patent [19]

Kibler et al.

[11] Patent Number: 5,114,734
[45] Date of Patent: May 19, 1992

[54] MUSHROOM FLAVORANT

[75] Inventors: Lawrence A. Kibler; Zdenek Kratky, both of New Milford; John S. Tandy, Litchfield, all of Conn.

[73] Assignee: Nestec S.A., Vevey, Switzerland

[21] Appl. No.: 188,360

[22] Filed: Apr. 29, 1988

Related U.S. Application Data

[63] Continuation-in-part of Ser. No. 45,608, May 1, 1987, abandoned.

[51] Int. Cl.$^5$ .............................................. A23L 1/226
[52] U.S. Cl. .................................... 426/650; 426/71; 426/49; 426/615
[58] Field of Search ....................... 426/650, 7, 49, 615

[56] References Cited

U.S. PATENT DOCUMENTS 3,100,153  8/1963  Knight et al.
4,275,081  6/1981  Coleman et al.

OTHER PUBLICATIONS

Chemical Abstracts, 103(15):121957w (Oct. 14, 1985).
Mattil et al., "Bailey's Industrial Oil and Fat Products", Interscience Publishers, 3rd ed. (1964), pp. 12-13, 210-13, 932-33, 936-37, 984-85.
Furia et al., Fenaroli's Handbook of Flavor Ingredients, 2nd ed., vol. 1 (1975), pp. 308-309.
Nomenclature Committee of the International Union of Biochemistry, "Enzyme Nomenclature", 1978, pp. 110-111.
B. O. de Lumen et al., "Formation of Volatile Flavor Compounds in Green Beans from Linoleic and Linolenic Acids", Journal of Food Science, 43 (1978), pp. 698-702, 708.
M. Wurzenberger et al., "The Formation of 1-octen-3-OL from the 10-Hydroperoxide Isomer of Linoleic Acid by a Hydroperoxide Lyase in Mushrooms (*Psalliota bispora*)", Biochimica et Biophysica Acta, 794, (1984), pp. 25-30.
M. Wurzenberger et al., "Stereochemistry of the Cleavage of the 10-Hydroperoxide Lyase from Mushrooms (*Psalliota bispora*)", Biochimica et Biophysica Acta, 795 (1984), pp. 163-165.
Tressl et al., "Formation of Eight-Carbon and Ten-Carbon Components in Mushrooms (*Agarious campestris*)", Journal of Agricultural Food Chemistry, 30 (1982), pp. 89-93.

*Primary Examiner*—Joseph Golian
*Attorney, Agent, or Firm*—Vogt & O'Donnell

[57] ABSTRACT

A mushroom flavorant is prepared by contacting homogenized mushrooms in an aqueous medium with a water-soluble salt of linoleic acid and with oxygen. The flavorant may be further enhanced by adding carob bean extract to the treated homogenate. The treated homogenate may be combined with carriers and other additives and spray-dried.

13 Claims, No Drawings

MUSHROOM FLAVORANT

CROSS-REFERENCE TO RELATED APPLICATION

This is a continuation-in-part application of Ser. No. 07/045,608, filed May 1, 1987 and now abandoned.

BACKGROUND OF THE INVENTION

The present invention relates to a mushroom flavor and more particularly to the preparation of a natural mushroom flavorant composition for imparting mushroom flavor to foodstuffs.

A characteristic and major volatile flavoring component of many mushroom species has been identified as being provided by 1-octen-3-ol which has been characterized as "mushroom alcohol", as referred to by B.O. de Lumen, et al., Journal of Food Science, 43:698–702, 708 (1978). That disclosure indicates that linoleic acid is a precursor for 1-octen-3-ol and that 1-octen-3-one recovered from mushrooms can be reduced rapidly to 1-octen-3-ol.

Wurzenburger, et al., Biochimica et Biophysica Acta., 794:25–30 (1984), describe a photosensitized oxidation of linoleic acid in benzene into hydroperoxide isomers of linoleic acid and formation of 1-octen-3-ol catalysed by a protein fraction isolated from an extract of the mushroom Psalliota bispora. Wurzenburger, et al., Biochimica et Biophysica Acta. 795:163–165 (1984), describe incubation of a mushroom protein fraction containing hydroperoxide lyase activity with 10-hydroperoxy-trans-8,cis-octadecadienoic acid ("10-HPOD"). The protein fraction was also incubated with linoleic acid. Each reaction forms 1-octen-3-ol, but it also is disclosed that the hydroperoxide lyase cleaves the "S" enantiomer of 10-HPOD which has been photooxidized to provide a much higher percentage of the "R" enantiomer of 1-octen-3-ol.

Tressl, et al., Journal of Agricultural Food Chemistry 30:89–93 (1982), describe experiments with mushrooms homogenized in a phosphate buffer with added linoleic acid and report that the concentration of 1-octen-3-ol, as determined by analytical procedures, was increased "considerably." Experiments with mushrooms homogenized in a phosphate buffer with potassium linoleate also were performed, but there is no report of the presence of 1-octen-3-ol in the compounds obtained.

SUMMARY OF THE INVENTION

The present invention provides a process for producing a novel mushroom flavorant characterized by contacting a mushroom homogenate in an aqueous medium with a water-soluble salt of linoleic acid and with oxygen for treating the homogenate for obtaining the flavorant.

The present invention provides a mushroom flavorant much more potent than any mushroom flavorant heretofore known to us. When fresh mushrooms are contacted with a water-soluble salt of linoleic acid and with oxygen in an aqueous medium in accordance with this invention, a 1-octen-3-ol content of the mushroom homogenate may be obtained which is from 10 to 15 times higher than the 1-octen-3-ol content of the original mushrooms. The resulting homogenate has a potent mushroom flavor and aroma. We have found that when treating older, stored mushrooms in accordance with this invention, a 1-octen-3-ol content may be obtained which is from 20 to 100 times or more than that of the original mushrooms depending upon the age of the mushrooms; that is, the older the mushrooms, the greater the relative increase in 1-octen-3-ol content and enhancement of flavor and aroma. It should be noted, however, that, generally, a flavorant prepared from non-fresh mushrooms, that is, mushrooms which have been harvested more than 3 to 4 days previously and stored and refrigerated prior to processing, will not be as potent as a flavorant produced from a homogenate of fresh mushrooms treated in accordance with the present invention.

Our work also indicates that the process of the present invention provides some 2 to 2½ times greater 1-octen-3-ol content for a mushroom homogenate than can be obtained by contacting comparable mushrooms with linoleic acid and with oxygen, and this is on the order of about 10 times as much as the 1-octen-3-ol concentration reported by the above-noted Tressl reference for mushrooms homogenized with linoleic acid.

Advantageously, a mushroom homogenate is intimately contacted at least with a salt of linoleic acid during and by reason of the homogenization of mushrooms. The salt-contacted mushrooms may be contacted with the oxygen subsequently, the contact being achieved by intimate mixing during introduction of oxygen into the homogenate. Most advantageously, the mushrooms are homogenized in the presence of a salt of linoleic acid in an aqueous medium while introducing oxygen. Additionally, oxygen may be introduced in an aqueous medium before homogenizing and contacting the homogenate with the salt while continuing to introduce oxygen. If the oxygen is introduced before homogenization, there is the potential advantage of ensuring a good supply of oxygen in the aqueous medium for contact with the salt-contacted mushrooms.

DETAILED DESCRIPTION OF THE INVENTION

In a batch process, wherein homogenized mushrooms are contacted with a salt of linoleic acid while mushrooms are being homogenized in an aqueous medium and while introducing oxygen for contacting the salt-contacted mushrooms, the period for homogenization and introduction of oxygen and contact may be for from about 1 minute to about 20 minutes, preferably for from about 2.5 minutes to about 15 minutes, and most preferably, for from about 5 minutes to about 12.5 minutes. The homogenization is performed such as in a high speed mixer for assuring comminution of the mushrooms and intimate contact of the homogenate, salt and oxygen. Preferably, in this embodiment, the salt of linoleic acid is introduced and dispersed in the aqueous medium, i.e., water, in a homogenizing means first, and then the mushrooms are added and oxygen is introduced while homogenization proceeds, although the oxygen may be introduced into the salt-containing aqueous medium prior to addition of the mushrooms. The mushrooms then are homogenized and thus contacted with the salt while oxygen is continued to be introduced for the time periods discussed above.

Alternatively, the mushrooms may be homogenized first in an aqueous medium for about a second to about 30 seconds and then be contacted with the salt of linoleic acid and then with oxygen, although it is more preferable and practical to contact the homogenate with at least the salt when homogenizing. However, to achieve optimum results when the mushrooms are first homogenized without contact with the salt or the salt and oxygen, the homogenate should be contacted with at least the salt within about, preferably, one minute and more preferably within about 30 seconds after being homogenized. This embodiment may be practiced in at least a semi-continuous fashion by first homogenizing the mushrooms in an aqueous medium and conveying the homogenate to be contacted within the relatively short time with at least the salt which, most conveniently, is introduced into the homogenate in a vessel into which the homogenate is conveyed for intimate mixing while introducing oxygen into the homogenate.

Alternatively, mushrooms are homogenized in an at least semi-continuous process in the presence of a aqueous medium containing the salt of linoleic acid for from about 1 to about 30 seconds, for example, and then transferred to a separate reaction vessel for contact with the oxygen by intimately mixing for a period of time for from about 1 minute to about 10 minutes, for example, and preferably for from about 2.5 minutes to about 7.5 minutes. Preferably, the time span between homogenization and contact with the oxygen also is as short as possible.

The water-soluble salt of linoleic acid is conveniently the sodium or the potassium salt. Preferably, the water-soluble salt of linoleic acid is obtained by chemical or enzymatic hydrolysis of a vegetable oil in which linoleic acid occurs as glyceride. The hydrolyzed glyceride then is alkalised with NaOH or KOH, for example. Suitable vegetable oils are cottonseed, soybean, peanut, corn, sunflower seed, poppy seed, linseed and perilla oils, but safflower oil is especially advantageous. The hydrolysis of the vegetable oil may be carried out conveniently enzymatically using lipase of pancreatic or of microbiological origin, for instance.

The amount of the water-soluble salt of linoleic acid used may be from about 0.1 part to about 5 parts per 100 parts, preferably from 0.2 parts to 2.5 parts and especially from 0.25 parts to 1 part per 100 parts by weight of the mushrooms homogenized.

The mushroom source may be any of the commercially available cultivar of the Agaricaceae family such as *Agaricus bisporus, Agaricus bitorquis* or *Agaricus campestris*. Brown strains are slightly preferred. Although it is most advantageous to use the mushrooms when they are fresh soon after harvesting such as within from 1 day to preferably less than 3 days after harvesting, older mushrooms which have been stored and refrigerated also may be used because they retain their capacity to convert linoleic acid into 1-octen-3-ol, but the resulting flavorant will not be as potent as compared with flavorants prepared from the mushrooms when they are fresh.

Conveniently, the mushrooms are washed before use, for example, by means of a belt washer where the mushrooms are sprayed with water, optionally in the presence of sodium bisulphite. Immersion of the mushrooms in water for prolonged periods of time should be avoided as anaerobic conditions created under such circumstances cause the mushrooms to metabolise their own 1-octen-3-ol, and their capacity to convert linoleic acid to 1-octen-3-ol in subsequent homogenization is at least partially lost.

The weight ratio of the mushrooms to the aqueous medium may vary from 1:0.01 to 1:10, preferably, 1:0.1 to 1:5, more preferably, from 1:0.5 to 1:2.5 and especially from 1:1 to 1:2.

Preferably, air is introduced into the homogenate by forced aeration for providing the oxygen. The amount of air introduced into the mushroom homogenate may be, for example, at a rate from 1 m$^3$/min to 20 m$^3$/min, and preferably, from 2 m$^3$/min to 10 m$^3$/min per 600 kg of homogenate. A mixture of oxygen and inert gases, e.g., carbon dioxide, nitrogen, may be used also instead of air.

The homogenization is preferably carried out at a temperature from about 12° C. to below 30° C., preferably from 12° C. to 28° C., and especially from about 15° C. to about 25° C.

The pH during the homogenization is advantageously from 5.5 to 8.0.

The homogenate may be spray-dried by conventional means, but preferably, at least one additive including flavoring plant extracts, edible oils and carriers suitable for spray drying are added to the treated homogenate. After mixing and homogenizing the additives with the treated homogenate, the resulting homogenate is preferably pasteurized by conventional means before being spray-dried.

The amount of flavoring plant extract added may be from about 0.1% to about 10%, preferably from 0.5% to 5% and especially from 1% to 4% by weight based on the weight of mushrooms homogenized. Although various flavoring plant extracts can be utilized, carob bean extract, also known as locust bean extract and commonly known as St. John's bread, which is an extract derived from the fruit of *ceratonia siliqua* (carob tree), a tree native to the Mediterranean area, provides a base note and superior fullness to the flavor of the mushroom homogenate, as compared with other flavoring plant extracts, together with providing the expected sweetness. Thus, the carob extract compliments the high notes of the mushroom flavor and adds fullness which provides a further improved and superior flavor to the treated mushroom homogenate.

The edible oil may be of vegetable or animal origin and may be added in amounts ranging from about 0.1% to about 15%, preferably from 0.2% to 10% and especially from 0.5% to 6% by weight based on the weight of the mushrooms homogenized. Particularly suitable oils are partially hydrogenated cottonseed oil and soya oil. The amount of carrier used may be from about 10% to about 200%, and preferably from 20% to 100% by weight based on the weight of the treated mushrooms. Examples of suitable carriers are low DE maltodextrin, high DE maltodextrins, modified starches, or gums such as gum arabic.

EXAMPLES

The following Examples further illustrate the present invention.

EXAMPLE I

Gum arabic (1.5 kg), sodium chloride (0.75 kg) and calcium chloride (0.37 kg) are dissolved in 150 kg of water. 15 kg safflower seed oil (high linoleic acid type), are added and the mixture is emulsified by means of a high speed mixer. The pH of the emulsion is maintained at 8 and the temperature at 40° C. Pancreatic lipase (0.37 kg, 92500 lipase unit) is added to the emulsion which is stirred and the pH is kept at around 8 by the addition of NaOH solution. The endpoint of the reaction is indicated by no further changes in the pH of the mixture. HCl is then added to bring the pH to 2.5. The mixture is allowed to stand to allow phase separation. The upper phase, containing fatty acids, is separated, 30 kg of water are added and the pH is adjusted to 9.4 by the addition of NaOH to give a solution containing approximately 10 kg of sodium linoleate.

An amount of this solution which contains 2 kg of sodium linoleate (i.e., one fifth of the total) is added to 400 liters of water at 20° C. in a 1000 liter high speed mixer equipped with an air sparger and the mixture is kept well dispersed. 400 kg of washed mushrooms (*Agaricus bisporus*) are added and the mixture is homogenized for 10 minutes at high speed with air introduced through the air sparger.

The homogenate is then mixed with 16.4 kg of vegetable oil, 166.4 kg of modified starch and 166.4 kg of low DE maltodextrin. After mixing this slurry, it is homogenized at 2000 psi, pasteurized and spray-dried and provides an attractive mushroom flavor. The concentration of 1-octen-3-ol is 1000 ppm.

EXAMPLE II

A similar procedure to that described in Example I is followed except that after homogenization of the mushrooms with the sodium linoleate, the homogenate is mixed with 10.0 kg of solid plant extract of carob bean in addition to the vegetable oil, modified starch and low DE maltodextrin. After mixing, the slurry is homogenized, pasteurized and spray-dried as in Example I.

The flavor obtained has an exceptionally desirable overall sweet mushroom flavor and has significant background or base notes and more fullness of flavor as compared with the flavor of the product of Example I which imparts primarily only high notes of a mushroom flavor.

COMPARATIVE EXAMPLE

A similar procedure to that described in Example I is followed except that, instead of the solution containing 2 kg of sodium linoleate, 2 kg of linoleic acid are used. The linoleic acid is added to the water and vigorously mixed in an in-line mixer to obtain an emulsion which is transferred to a vessel for addition of oxygen and mushrooms as in Example I.

The concentration of the 1-octen-3-ol in the spray-dried product is only 400 ppm and the product is much less potent than the flavorant of Example I.

Similar results also are obtained when linoleic acid is utilized and the procedures and the homogenization and contacting are performed as in Example I.

We claim:

1. A process for increasing the 1-octen-3-ol content of mushrooms for producing a mushroom flavorant comprising contacting a mushroom homogenate in an aqueous medium with a water-soluble salt of linoleic acid and with oxygen introduced into the homogenate for treating the homogenate for obtaining the flavorant.

2. A process according to claim 1 wherein mushrooms are homogenized first in the presence of the salt of linoleic acid in the aqueous medium for contacting the salt with the homogenate, and then the homogenate is contacted with the oxygen introduced into the homogenate, wherein the salt is in an amount of from 0.1 part to about 5 parts per 100 parts by weight of mushrooms homogenized, wherein the mushrooms are homogenized for from about 5 seconds to about 30 seconds and wherein oxygen is introduced and contacted with the homogenate for from about 1 minute to about 10 minutes at a temperature of from about 12° C. to below 30° C.

3. A process according to claim 1 wherein mushrooms are homogenized in the presence of the salt of linoleic acid in the aqueous medium while the oxygen is introduced for contacting the homogenate, wherein the salt is in an amount of from 0.1 part to 5 parts per 100 parts by weight of mushrooms homogenized and wherein the mushrooms are homogenized and the oxygen is introduced and contacted with the homogenate for from about 1 minute to about 20 minutes at a temperature of from about 12° C. to below 30°.

4. A process according to claim 1 wherein the salt of linoleic acid is selected from the group consisting of a sodium and a potassium salt of linoleic acid.

5. A process according to claim 1 wherein air is introduced into the homogenate by forced aeration at a rate of from 1 $m^3$/min to 20 $m^3$/min per 600 kg of homogenate for providing the oxygen which is introduced into and contacted with the homogenate.

6. A process according to claim 1 further comprising adding at least one of a flavoring plant extract additive, of an edible oil additive and of a carrier additive suitable for spray drying to the treated homogenate.

7. A process according to claim 6 wherein the flavoring plant extract additive is added in an amount from about 0.1% to about 10% by weight based upon the weight of mushrooms homogenized, the edible oil additive is added in an amount of from about 0.1% to about 15% by weight based upon the weight of mushrooms homogenized and the carrier additive is added in an amount of from about 10% to about 75% by weight based upon the weight of mushrooms homogenized.

8. A process according to claim 1 wherein at least one additive which comprises at least a carob bean extract is added to the treated homogenate.

9. A process according to claim 1 further comprising spray-drying the treated homogenate.

10. A process according to claim 6 or 8 further comprising spray drying the treated homogenate and the at least one additive.

11. A process according to claim 1 further comprising hydrolyzing a vegetable oil in which linoleic acid occurs as a glyceride, then alkalizing the hydrolyzed glyceride to obtain the linoleic acid salt.

12. The product of the process of claim 1 or 2 or 3 or 8 or 9.

13. The product of the process of claim 10.

* * * * *